(12) United States Patent
Flippin et al.

(10) Patent No.: US 11,903,590 B1
(45) Date of Patent: Feb. 20, 2024

(54) TRAUMA DRESSING ARTICLE FOR JUNCTIONAL INJURIES

(71) Applicant: MARCHBALL LLC, Cleveland, OH (US)

(72) Inventors: James Alford Flippin, Cleveland, OH (US); Hillary Ann Duchnowski, Lakewood, OH (US)

(73) Assignee: MARCHBALL LLC, Cleveland, OH (US)

( * ) Notice: Subject to any disclaimer, the term of this patent is extended or adjusted under 35 U.S.C. 154(b) by 0 days.

(21) Appl. No.: 17/971,111

(22) Filed: Oct. 21, 2022

(51) Int. Cl.
*A61B 17/132* (2006.01)
*A61B 17/12* (2006.01)
*A61B 17/00* (2006.01)

(52) U.S. Cl.
CPC .............................. *A61B 17/1325* (2013.01); *A61B 2017/00862* (2013.01); *A61B 2017/00884* (2013.01); *A61B 2017/00951* (2013.01); *A61B 2017/12004* (2013.01)

(58) Field of Classification Search
CPC ...... A61B 17/1325; A61B 2017/00862; A61B 2017/00884; A61B 2017/00951; A61B 2017/12004; A61F 15/001; A61F 17/00; A61F 2013/00463; A61F 2013/00468; A61F 2013/00472; A61F 2013/00902; A61F 13/00; A61F 13/069
See application file for complete search history.

(56) References Cited

U.S. PATENT DOCUMENTS

| 5,307,811 A * | 5/1994 | Sigwart ................ A61B 17/132 600/490 |
| 5,939,339 A * | 8/1999 | Delmore ................ A61L 15/30 602/76 |
| 9,226,846 B2 * | 1/2016 | Parssinen ................ A61F 5/05 |
| 2005/0165445 A1 * | 7/2005 | Buckman ................ A61F 13/00 606/213 |
| 2007/0260165 A1 * | 11/2007 | Johnson ................ A61F 15/006 602/41 |
| 2012/0232578 A1 * | 9/2012 | Altobelli ............... A61B 17/135 606/202 |
| 2014/0228732 A1 * | 8/2014 | Steinbaugh .......... A61B 17/135 602/53 |
| 2018/0193010 A1 * | 7/2018 | Riebman ............... A61L 24/001 |

OTHER PUBLICATIONS

Oxford Dictionary, 2015, Oxford English Dictionary, https://www.oed.com/view/Entry/12699?rskey=FHZoQK&result=1&isAdvanced=false#eid (Year: 2015).*

* cited by examiner

*Primary Examiner* — Sarah W Aleman
*Assistant Examiner* — Mikail A Mannan
(74) *Attorney, Agent, or Firm* — The Concept Law Group, PA; Scott D. Smiley; Scott M. Garrett

(57) ABSTRACT

A trauma dressing article includes a body on which a cap of absorbent material is disposed. A wrap strip is attached to the body at one end of the wrap strip. The trauma dressing article is particularly suited for treating wounds at junctional locations of the body (e.g. armpits, groin) to prevent exsanguination. The body of the article is oriented such that the absorbent material is positioned towards the wound site, and then the body is moved to press the absorbent material into the wound site. The wrap strip is then wrapped around portions of the injured person's body and over the article to create an inward pressure against the wound site.

16 Claims, 13 Drawing Sheets

TRAUMA DRESSING ARTICLE FOR JUNCTIONAL INJURIES

FIELD OF THE INVENTION

The present invention relates generally to trauma wound dressings intended to stop or substantially reduce bleeding due to laceration or penetrating traumas such as gunshot wounds or stab wounds, and, more particularly, relates to a wound dressing article that is particularly suited to use in junctional injuries that are not suitably addressed by a tourniquet, such as in the groin or armpit. The wound dressing article is a ball-like body having approximately one hemisphere made of, coated with, or comprising a wound dressing material, and a wrap connected to the device body that can be wrapped around the injured person's body and over the wound dressing article to create pressure against the injury location.

BACKGROUND OF THE INVENTION

Severe laceration, penetrating, or dismemberment injuries to limbs are commonly addressed by use of a tourniquet in order to stop bleeding and prevent death due to blood loss. Junctional injuries are those that occur at the junction of a limb or limbs with the body. The groin and armpit regions, in particular, are junctional locations. When a person suffers an injury at these junctional locations that threatens to result in a critical loss of blood, a standard/traditional tourniquet is unsuitable to address the injury. Such junctional injuries care is instead best addressed by direct pressure and clotting agents. However, it is not practical for a trauma responder to continuously apply pressure to a person's injury until that person can get to more comprehensive trauma care.

Therefore, a need exists to overcome the problems with the prior art as discussed above.

SUMMARY OF THE INVENTION

In accordance with some embodiments of the inventive disclosure, there is provided a trauma dressing article for junctional injuries that includes a body, a gauze cap formed over at least a portion of the body and attached to the body, and a wrap strip having a first end that is attached to the body, and which extends from the body.

In accordance with a further feature, the body is made of a resilient material.

In accordance with a further feature, the body is spherical.

In accordance with a further feature, the body includes a first hemisphere and a second hemisphere, wherein the second hemisphere has a radius that is smaller than a radius of the first hemisphere, and wherein the gauze cap covers the second hemisphere and does not extend significantly over the first hemisphere.

In accordance with a further feature, the wrap strip is self-adhering.

In accordance with a further feature, the wrap strip is elastic.

In accordance with a further feature, the wrap strip is provided in a rolled configuration.

In accordance with a further feature, the wrap strip is at least four feet long.

In accordance with a further feature, the first end of the wrap strip is glued to the body.

In accordance with a further feature, the gauze cap contains a clotting agent that is at least one of kaolin, chitosan, or recombinant activated human clotting factors.

In accordance with a further feature, the gauze cap includes a dressing tail comprising a free section of dressing material that extends freely from the gauze cap.

In accordance with some embodiments of the inventive disclosure, there is provided a packaged trauma dressing article that includes a body having at least a portion of which that is made of a resilient material and which presents a rounded outer surface. The trauma dressing article further includes a gauze cap disposed on the portion of the body made of the resilient material, a wrap strip including a sheet strip of dressing wrap, and a packaging in which the body, gauze cap, and wrap strip are disposed and sealed.

In accordance with a further feature, the packaging is vacuum sealed.

In accordance with a further feature, wherein the body is spherical, and includes a first hemisphere and a second hemisphere, wherein the second hemisphere has a radius that is smaller than a radius of the first hemisphere, and wherein the gauze cap covers the second hemisphere and does not extend significantly over the first hemisphere.

In accordance with a further feature, the wrap strip is provided in a rolled configuration.

In accordance with some embodiments of the inventive disclosure, there is provided a trauma dressing article for use in junctional injuries to prevent exsanguination that includes a body having a rounded outer surface, an absorbent covering disposed over at least a portion of the body and over the rounded outer surface, and a wrap strip attached to the body which has a portion that extends from the body to a free end of the wrap strip.

In accordance with a further feature, the body is the body is made of a resilient material and is spherical, and includes a first hemisphere and a second hemisphere, wherein the second hemisphere has a radius that is smaller than a radius of the first hemisphere, and wherein the absorbent covering covers the second hemisphere and does not extend significantly over the first hemisphere.

In accordance with a further feature, the absorbent covering is a gauze cap that includes a dressing tail comprising a free section of dressing material that extends freely from the gauze cap.

In accordance with a further feature, the gauze cap contains a clotting agent that is at least one of kaolin, chitosan, or recombinant activated human clotting factors.

In accordance with a further feature, the wrap strip is elastic, self-adhering, and configured in a roll.

Although the invention is illustrated and described herein as embodied in a trauma dressing article for treating junctional injuries, it is, nevertheless, not intended to be limited to the details shown because various modifications and structural changes may be made therein without departing from the spirit of the invention and within the scope and range of equivalents of the claims. Additionally, well-known elements of exemplary embodiments of the invention will not be described in detail or will be omitted so as not to obscure the relevant details of the invention.

Other features that are considered as characteristic for the invention are set forth in the appended claims. As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one of ordinary skill in the art to variously employ the present invention in virtually any appropriately detailed structure. Further, the terms and phrases used herein are not intended to be limiting; but rather, to provide an understandable description of the invention. While the specification concludes with claims defining the features of the invention that are regarded as novel, it is believed that the invention will be better understood from a consideration of the following description in conjunction with the drawing figures, in which like reference numerals are carried forward. The figures of the drawings are not drawn to scale.

Before the present invention is disclosed and described, it is to be understood that the terminology used herein is for the purpose of describing particular embodiments only and is not intended to be limiting. The terms "a" or "an," as used herein, are defined as one or more than one. The term "plurality," as used herein, is defined as two or more than two. The term "another," as used herein, is defined as at least a second or more. The terms "including" and/or "having," as used herein, are defined as comprising (i.e., open language). The term "coupled," as used herein, is defined as connected, although not necessarily directly, and not necessarily mechanically. The term "providing" is defined herein in its broadest sense, e.g., bringing/coming into physical existence, making available, and/or supplying to someone or something, in whole or in multiple parts at once or over a period of time.

"In the description of the embodiments of the present invention, unless otherwise specified, azimuth or positional relationships indicated by terms such as "up", "down", "left", "right", "inside", "outside", "front", "back", "head", "tail" and so on, are azimuth or positional relationships based on the drawings, which are only to facilitate description of the embodiments of the present invention and simplify the description, but not to indicate or imply that the devices or components must have a specific azimuth, or be constructed or operated in the specific azimuth, which thus cannot be understood as a limitation to the embodiments of the present invention. Furthermore, terms such as "first", "second", "third" and so on are only used for descriptive purposes, and cannot be construed as indicating or implying relative importance.

In the description of the embodiments of the present invention, it should be noted that, unless otherwise clearly defined and limited, terms such as "installed", "coupled", "connected" should be broadly interpreted, for example, it may be fixedly connected, or may be detachably connected, or integrally connected; it may be mechanically connected, or may be electrically connected; it may be directly connected, or may be indirectly connected via an intermediate medium. As used herein, the terms "about" or "approximately" apply to all numeric values, whether or not explicitly indicated. These terms generally refer to a range of numbers that one of skill in the art would consider equivalent to the recited values (i.e., having the same function or result). In many instances these terms may include numbers that are rounded to the nearest significant figure. In this document, the term "longitudinal" should be understood to mean in a direction corresponding to an elongated direction of the article being referenced. Those skilled in the art can understand the specific meanings of the above-mentioned terms in the embodiments of the present invention according to the specific circumstances.

BRIEF DESCRIPTION OF THE DRAWINGS

The accompanying figures, where like reference numerals refer to identical or functionally similar elements throughout the separate views and which together with the detailed description below are incorporated in and form part of the specification, serve to further illustrate various embodiments and explain various principles and advantages all in accordance with the present invention.

DETAILED DESCRIPTION

Figure 1:
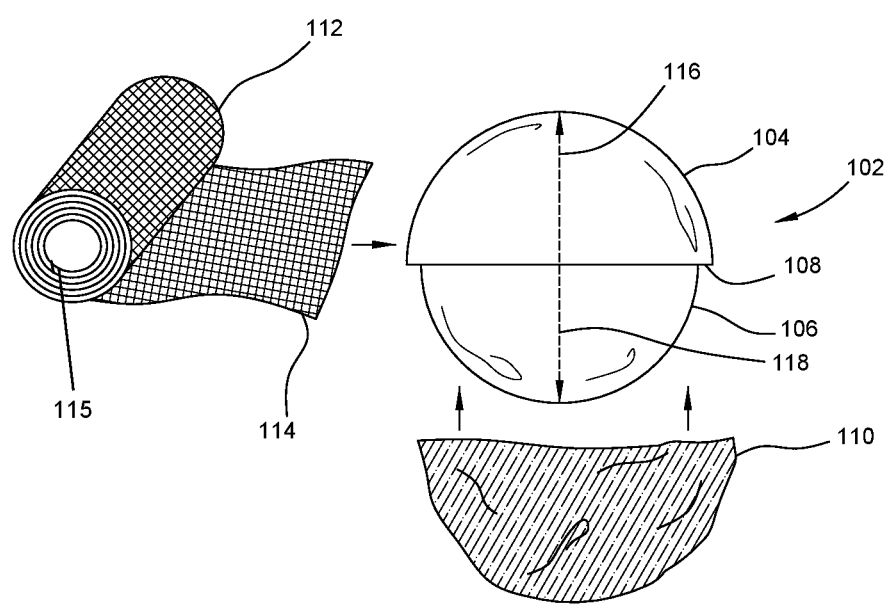
FIG. 1 is an exploded view of a trauma dressing article for junctional injuries, in accordance with some embodiments.

While the specification concludes with claims defining the features of the invention that are regarded as novel, it is believed that the invention will be better understood from a consideration of the following description in conjunction with the drawing figures, in which like reference numerals are carried forward. It is to be understood that the disclosed embodiments are merely exemplary of the invention, which can be embodied in various forms.

Figure 2:
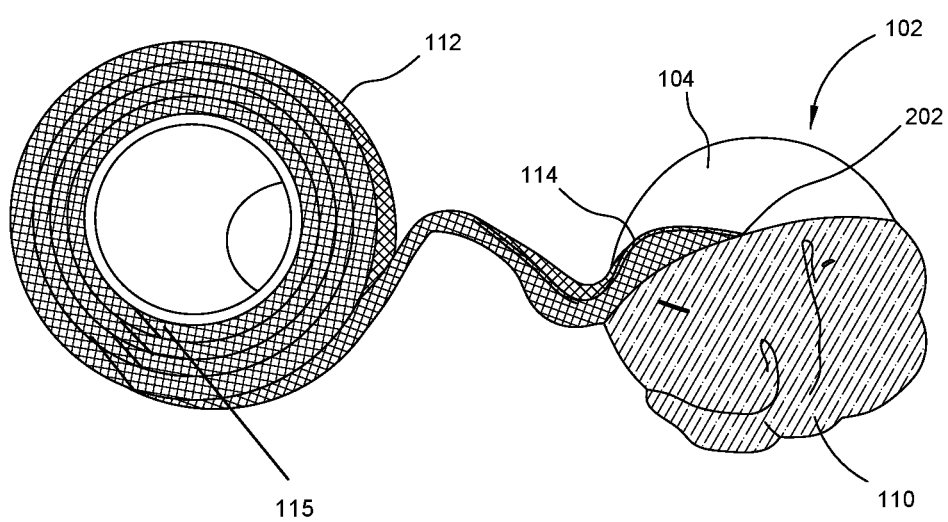
FIG. 2. is a side view of a trauma dressing article for junctional injuries, in accordance with some embodiments.
Figure 3:
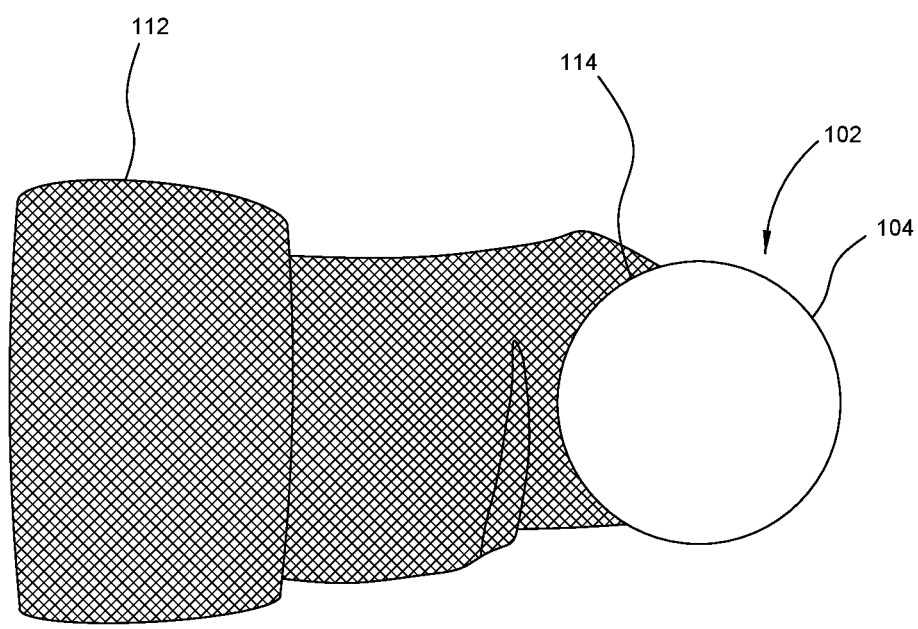
FIG. 3 is a top view of a trauma dressing article for junctional injuries, in accordance with some embodiments.
Figure 4:
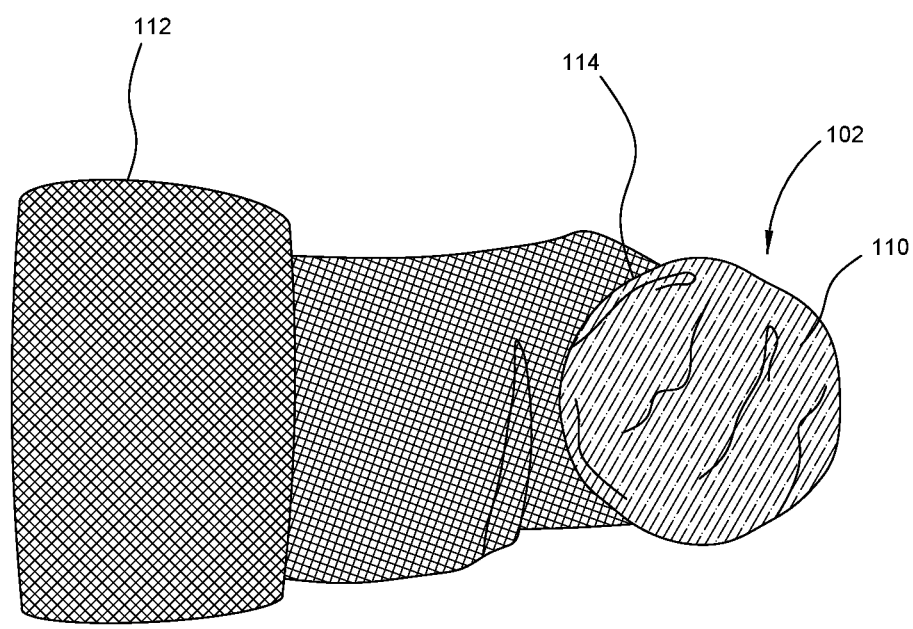
FIG. 4 is a bottom view of a trauma dressing article for junctional injuries, in accordance with some embodiments.

FIG. 1 is an exploded view of a trauma dressing article 100 for junctional injuries, in accordance with some embodiments. FIGS. 2-4 show other views of the trauma dressing article 100 that can referenced in the following description. A junctional injury is an injury that has occurred at the junction of a limb or limbs with the torso. Examples of junctional regions include the groin and armpits. Injuries at these regions that threaten exsanguination cannot be treated by use of a standard/traditional tourniquet. Injuries can include, for example, gunshot wounds and deep lacerations. In order to prevent exsanguination, pressure on the wound is required. The trauma dressing article 100 is configured to be applied in a way that will maintain pressure on wounds in these sorts of locations, and prevent excess blood loss.

The trauma dressing article 100 includes a body 102 that can include a first portion 104 and a second portion 106. A gauze cap 110 is affixed to the to body 102 and covers at least a portion of the body 102. In some embodiments the gauze cap 110 can cover about half of the body 102, although in some other embodiments the entire body 102 can be covered by gauze or a gauze cap 110. The gauze cap 110 can include more than, for example, a single layer of gauze placed on the body. When actual gauze is used, there should be several layers, as would be used in a gauze pad designed to be applied to bleeding wounds. As is well known, medical gauze is a woven fabric made typically made of cotton. Those skilled in the art will appreciate that other medically suitable absorbent materials can be used equivalently. Thus, as used here, the term "gauze cap" will be understood to refer to a medically suitable absorbent covering of the body 102.

The portion of the body 102 on which the gauze cap 110 is affixed can have a rounded outer surface and is preferably compressible such that when the body is urged/pressed against a wound site that portion of the body 102 will deform somewhat to the contours of the body and the wound site. The gauze cap 110 is made of a hemostatic gauze which may contain substances such as kaolin, chitosan, or recombinant activated human clotting factors. It may also be made simply of an absorbent material that is suitable for application to a bleeding wound. The gauze cap 110 can be formed, for example, by feeding a strip of gauze into a mold, which has the negative shape of the portion of the body 102 to which the gauze cap will be attached, and then a medically suitable adhesive can be used to join the gauze cap to the body 102, providing several layers of gauze between the outside of the gauze cap 110 and the surface of the body 102 on which the gauze cap 110 is disposed. In another embodiment the gauze cap can be formed by layering sheets of gauze, placing the layered gauze over the body 102, and then cutting off excess gauze. In another embodiment, a roll of gauze can be formed having an inside diameter (or shape) that is equal the diameter (or shape) of the body 102, and the body 102 can be inserted into the gauze roll such that one end of the gauze roll can be adhered or affixed to the body, and the opposite end can be folded over and against the body, and glued or stapled in place. In an alternative form of connecting the gauze to the body 102, the body 102 can have cuts into the body 102 into which portions of the gauze cap 110 can be inserted. The resiliency of the material of the body 102 will hold those portions (or portion) by friction and retain them and the gauze cap 110 to the body. In addition to the gauze cap 110 there is a wrap strip 112 that has an end 114 which is attached to the body 102, such as by a medically suitable adhesive, or by a mechanical connection (e.g. fasteners, or being inserted into a portion of the body for frictional retention).

The wrap strip 112 is a strip of dressing wrap material that is wrapped around the patient's body after the gauze cap 110 is placed against the wound site. The dressing wrap material of the wrap strip 112 is therefore a sheet strip of pliant material like a fabric that can be initially gathered in a rolled configuration or equivalent gathering/bunching/folding configuration that allows a person to wrap the wrap strip 112 around the patient's body, and over the body 102 of the trauma dressing article 100 in order to put pressure on the body 102, and therefore against the wound site. The wrap strip 112 therefore has one end attached to the body 112, and another end 115 that is free (free end) and not attached to anything. In some embodiments the wrap strip 112 can be elastic to allow it to be stretched, thereby creating pressure against the body 102 as the material of the wrap strip 112 tends to elastically contract towards its original state upon being stretched. In some embodiments the wrap strip can be self-adhesive, so that, upon the distal end of the wrap strip 112 being exposed after wrapping the entire length of the wrap strip 112 around the patient's body (several times), the material of the wrap strip 112 will tend to stay in place due to the adhesiveness of the material between portions of the wrapped material in contact with each other, and the end can be tucked into the wrap or tied to the wrap, as is appropriate for a given injury treatment and patient. In some embodiments the wrap strip 112 can be at least four feet long from the first end 114 to the free end 115 of the wrap strip 112. In other embodiments the wrap strip 112 can have other lengths.

The gauze cap 110 generally conforms to the shape of the body 102. As shown there, the body can be spherical, or ball-shaped. In some embodiments the body 102 can be a generally spherical shape having a diameter of one and a half to three inches. This range is particularly suitable for armpit and groin injuries such as gunshot and stab wounds. In other embodiments the spherical body can be larger or smaller. The body 102 can be made of a resilient material, or be compressible with a tendency to return to its uncompressed state. Thus, the body 102 can be made of an elastic foam, or it can have a sealed gas (e.g. air) volume and a flexible exterior wall. By being resilient in this manner, when the body 102 is under pressure from the wrap strip 112, the body 102 can deform from its natural uncompressed state to conform to the body region where it is applied on the patient. That is, the portion of the body 102 facing the wound site (e.g. the gauze cap 110 side) will flatten or otherwise match the shape of the body portion it is pressed against. Of course, this pressure also acts to shape the skin and soft tissue, but any hard body portions (e.g. bones) cause the body 102 to conform around those hard body portions and still maintain pressure on the wound site. The seal of the wound site can also be improved in some embodiments by the inclusion of a clotting agent in the gauze cap 110. For example, chitosan and kaolin are known clotting agents that can be impregnated in the gauze cap 110 material.

The body 102 can be formed in a variety of shapes to conform to the shape of the various junctional body regions. However, a compressible, resilient, and generally spherical shaped body has good all-around application. The body 102 specifically shown in FIG. 1 is spherical, having a first portion 104 in the form of a hemisphere, and a second portion 106 in the form of a complementary hemisphere. However, the first hemisphere 104 has a radius 116 that is larger than the radius 118 of the second hemisphere 106, creating a shoulder 108 to which the gauze cap 110 and the first end 114 of the wrap strip 112 can be adhered using a medically suitable adhesive. It is contemplated that the body 102 can be made of multiple different materials, as well. For example, the second portion 106 can be made of a resilient, compressible material that can somewhat flatten out when pressure is applied to it (i.e. in the direction of radius 118), against a wound site. The first portion 104 can be made of a rigid material to which the second portion 106 is affixed, or even a rigid shell that fits over the second portion 106 (where the second portion 106 would be a full sphere). It is further contemplated that the surface of the first portion can be configured to provide good friction when wet so that if it gets wet (e.g. from blood), the person applying the trauma dressing article 100 can retain grip on the first portion even while wearing medical gloves. Texturing, grip features, and surface treatment are examples of features that can be used to ensure the treating personnel will have good purchase/grip on the body 102 when applying the trauma dressing article. The shoulder 108 can extend completely around the body 102. It is further contemplated that other body shapes can be used, including, for example, a cylindrical body shape where one side (in a direction along the cylinder axis) is covered in gauze or equivalent material. Such a body shape could be more suitable for use in applying pressure to an elongated laceration, for example. It is also contemplated that a cylindrical body could be cut to length by treating personnel to fit the body of the trauma dressing article to the patient's wound.

Figure 5:
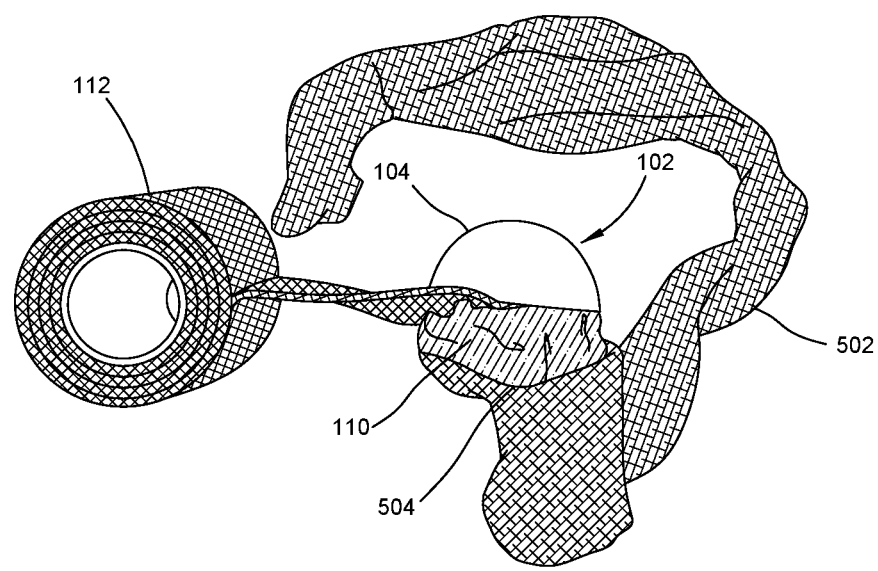
FIG. 5 is a side view of a trauma dressing article for junctional injuries having a dressing tail, in accordance with some embodiments.

FIG. 5 is a side view of a trauma dressing article 500 for junctional injuries having a dressing tail 502, in accordance with some embodiments. The dressing tail 502 is a free section of dressing material in addition to the gauze, which itself can be gauze, that is attached to the body 102 or the gauze cap 110 at an end 504 of the dressing tail 502. In some embodiments the dressing tail 504 can be a portion of the gauze dressing used to make the gauze cap 110 that simply continues from the gauze cap 110. The dressing tail 504 provides additional dressing material that can be used to pack a wound that may not be adequately covered or filled by just the gauze cap 110. The dressing tail 504 can have a variety of lengths and can be cut to a desired length by trauma personnel applying the trauma dressing article 500. The dressing tail 504 can, in some embodiments, include a clotting agent to facilitate clotting after the trauma dressing article 500 has been applied.

Figure 6:
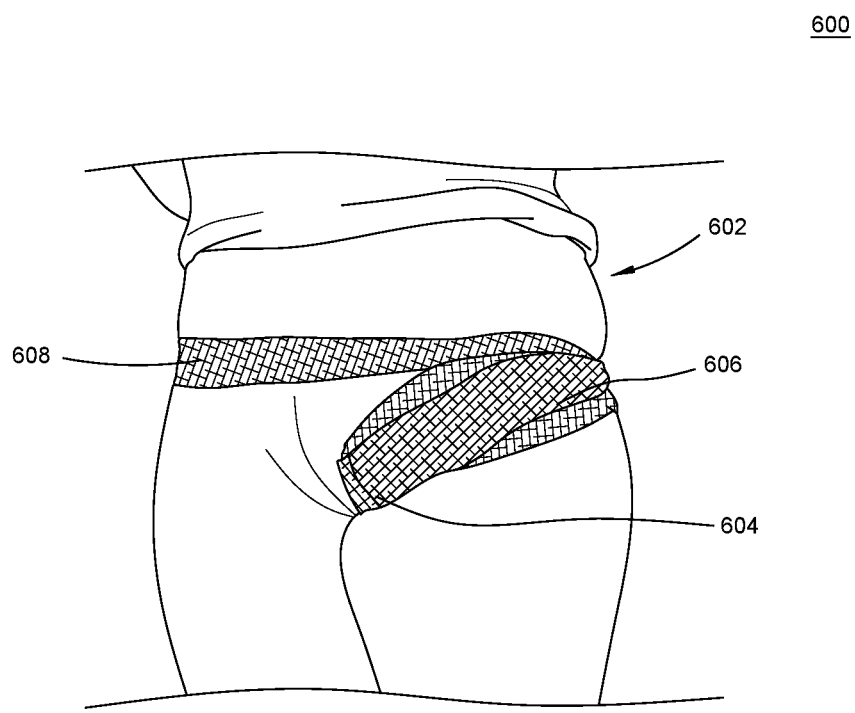
FIG. 6 shows the application of a trauma dressing article for an injury in a groin region, in accordance with some embodiments.
Figure 7:
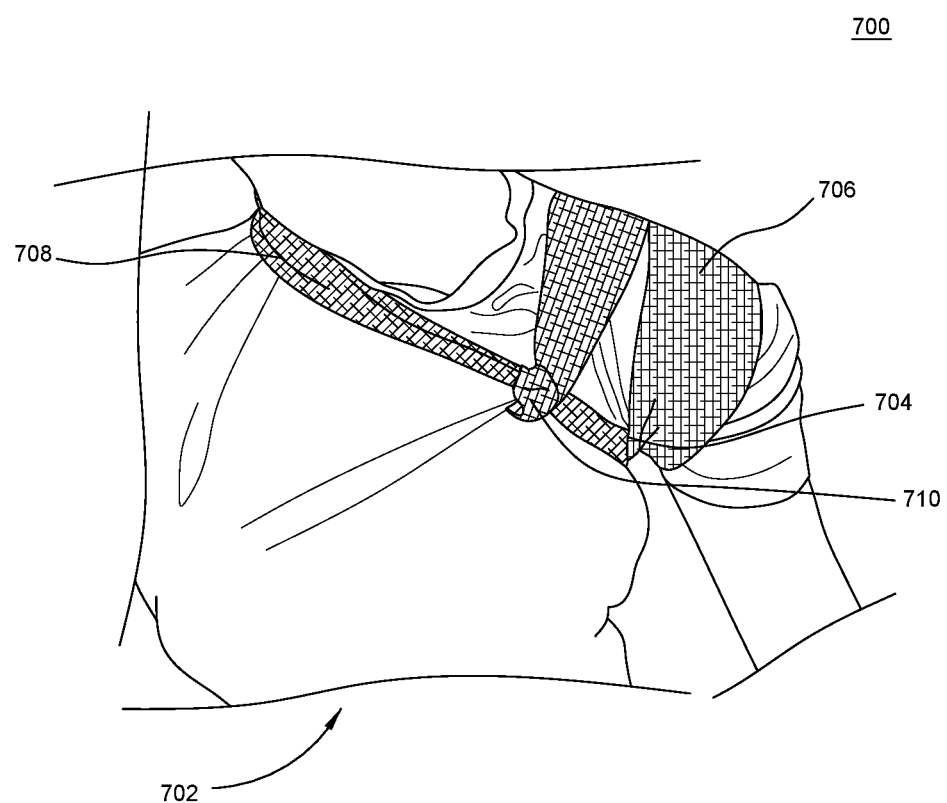
FIG. 7 shows the application of a trauma dressing article for an injury in an armpit region, in accordance with some embodiments.

FIGS. 6-7 show examples of applying a trauma dressing article in junctional regions using a trauma dressing article as shown in FIGS. 1-5 (a dressing tail may or may not be included). However, because the wrap strip is wrapped over the body of the trauma dressing article (and around the body of the patient), the body of the trauma dressing article is not in view. The wrap strip is typically wrapped over the body of the trauma dressing article several times in order to create the inward pressure against the wound site, which conceals the body of the trauma dressing article.

FIG. 6 shows the application 600 of a trauma dressing article for an injury in a groin region 604 of a person 602, in accordance with some embodiments. In this example the body of the trauma dressing article is position in the groin region 604 with the gauze cap being placed into a wound site. Once the body of the trauma dressing article is in place, the wrap strip is wrapped in a primary wrap 606 around the person's upper thigh and buttock, and over the body of the trauma dressing article, at least twice. If the wrap strip is elastic, it can be stretched by the person applying the trauma dressing article to create tension against the body of the trauma dressing article. A secondary wrap 608 can be wrapped around the person's pelvis to provide another axis of control of the wrap strip and secure the primary wrap 606 in place.

FIG. 7 shows the application 700 of a trauma dressing article for an injury in an armpit region 704 of a person 702, in accordance with some embodiments. In this application the wrap strip is used to create a primary wrap 706 around the injured person's shoulder and armpit. It should be clear to those having skill in applying trauma dressings, but the wrap strip is routed, initially, from the body of the trauma dressing article at its location in the armpit, with the gauze cap pressed into the wound site, up over the shoulder on one side of the person's body, and then down over the other side of the person's body to the armpit 702, back across the armpit 702 and over the body of the trauma dressing article to the first side of the person's body. Again, at least two windings of the wrap, while the wrap strip is being pulled or stretched taut. A secondary wrap 708 passes from the armpit region 702 across the person's chest and up to their neck on the opposite side of the neck from the injured armpit region 702, and then around the person's back to the injured armpit 702. Again, several windings of the wrap strip can be used for the secondary wrap 708. The order or the wrapping can also be changed so that the secondary wrap 708 is wound first, and then the primary wrap 706 is completed. The winding of the wrap strip can also be alternated between the two wraps 706, 708. The end of the wrap strip can be tied in a knot 710 to one or both of the wraps 706, 708 to secure it in place. Each of the two wraps 706, 708 impart force in different directions against the body of the trauma dressing article, pressing the gauze cap into the wound site. By having two different directions of force, the body of the dressing article is stabilized and resists moving around relative to the wound site.

Figure 8:
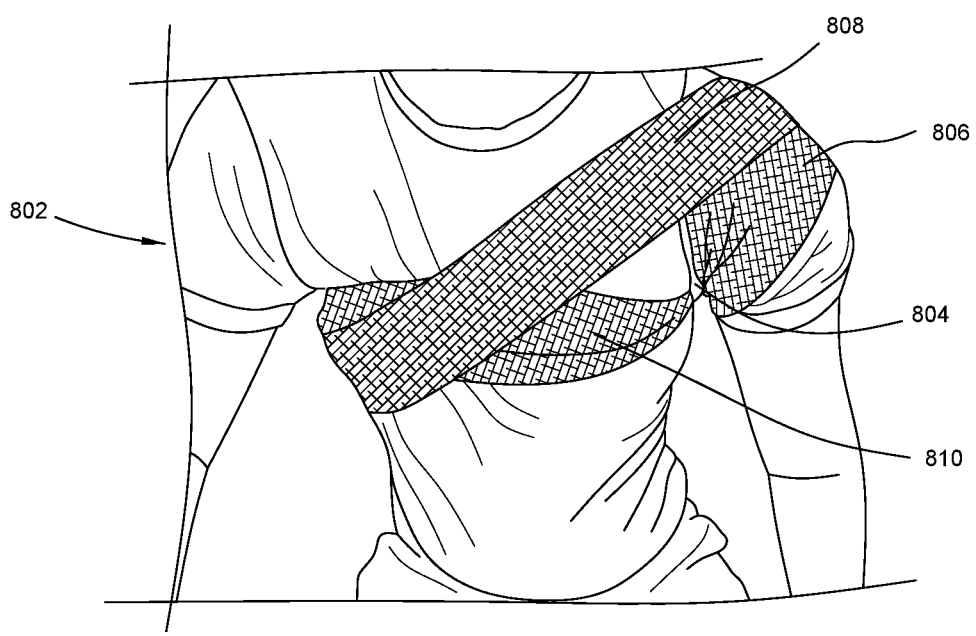
FIG. 8 shows the application of a trauma dressing article for an injury in an armpit region, in accordance with some embodiments.

FIG. 8 shows an alternative application 800 of a trauma dressing article for an injury in an armpit region 804 of a person 802, in accordance with some embodiments. As with application 700, the gauze cap of the trauma dressing article is first placed against and into the wound site in the armpit 804. A first wrap 806 can then be wound around the person's shoulder and armpit, with each winding passing over and against the body of the trauma dressing article, under tension provided by the person doing the wrapping with the wrap strip. After at least two windings of the wrap strip are in place, and cross chest wrap 808 can be used to route the wrap strip around the upper chest and armpit 704 of the person in s second wrap 810. Again, this configuration of wraps/windings creates pressure against the body of the trauma dressing article, which creates pressure against and into the wound site, and provides that pressure from two different general directions to stabilize the body of the trauma dressing article relative to the wound site and help keep it in place until additional trauma care can be rendered.

Figure 9A:
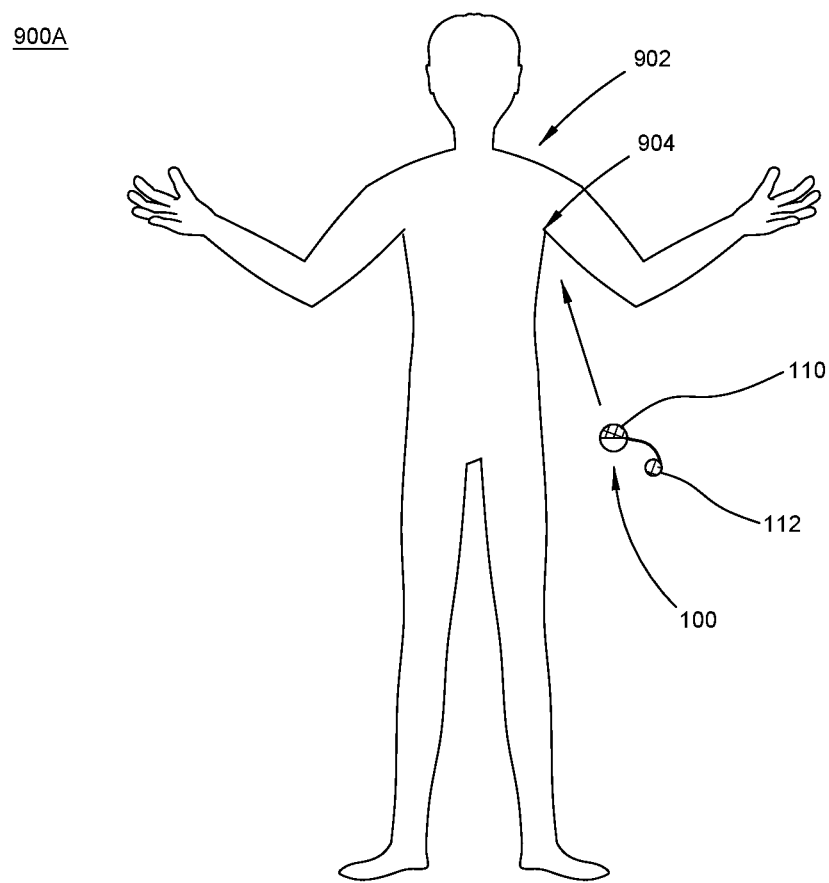
FIGS. 9A-9C show a sequence of applying the trauma dressing article to a junctional injury, in accordance with some embodiments.
Figure 9B:
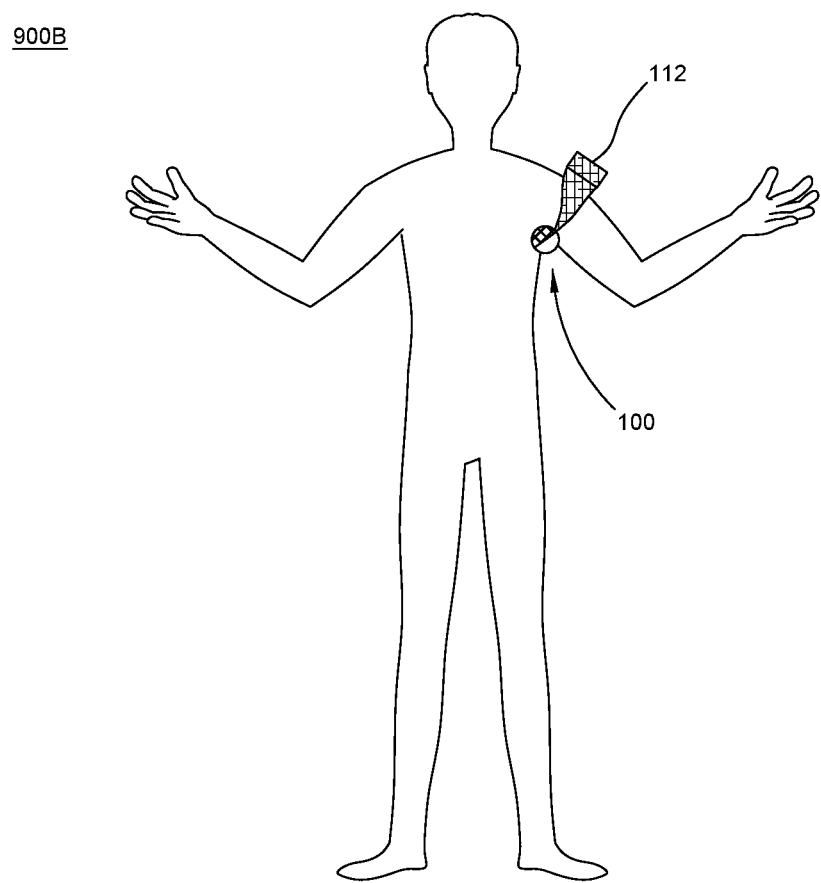
Figure 9C:
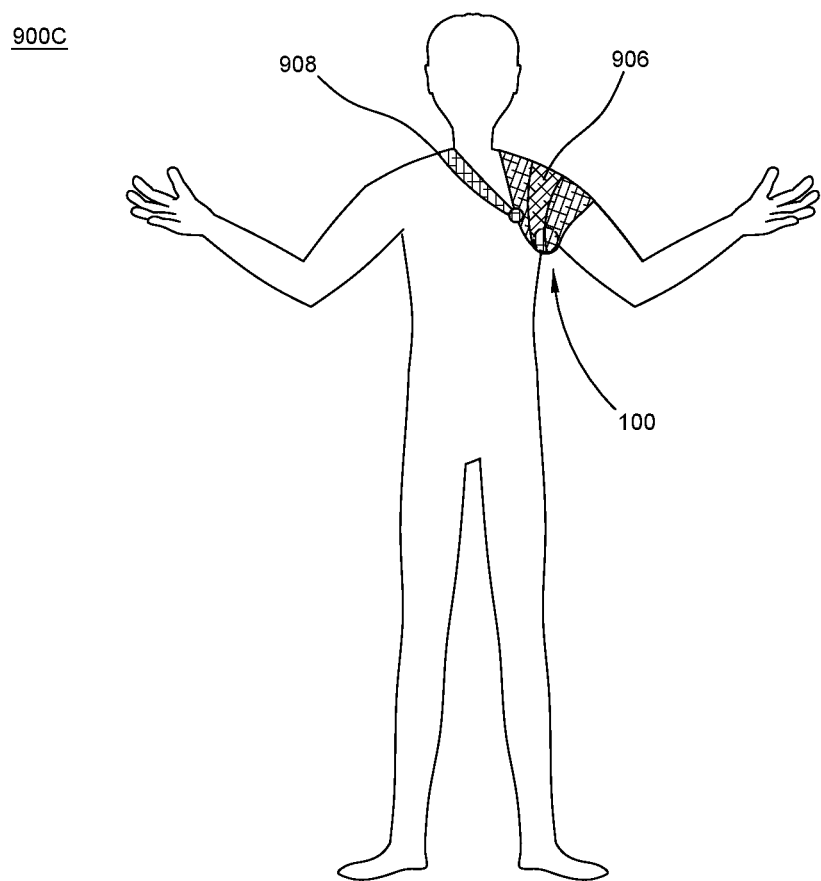

FIGS. 9A-9C show a sequence 900A-900C of applying the trauma dressing article 100 to a junctional injury, in accordance with some embodiments. In particular, the application 700 is shown to address a junctional injury wound site 904 in the left armpit of a person 902. In 900A the trauma dressing article 100 is applied by orienting the gauze cap 110 toward the wound site 904. The wrap strip 112 is ready to be wound around the person's shoulder and upper chest. In 900B the body of the trauma dressing article is pressed against the wound site, and in particular the gauze cap is pressed into/against the wound site. The wrap strip 112 is then wound up over the person's shoulder and around the shoulder and armpit several times, covering the body of the trauma dressing article. In 900C the primary wrap 906 and secondary wrap 908 are complete (equivalent to 706, 708, respectively). The body of the trauma dressing article is completely covered by the wrap strip windings, resulting in pressure against the wound site.

Figure 10:
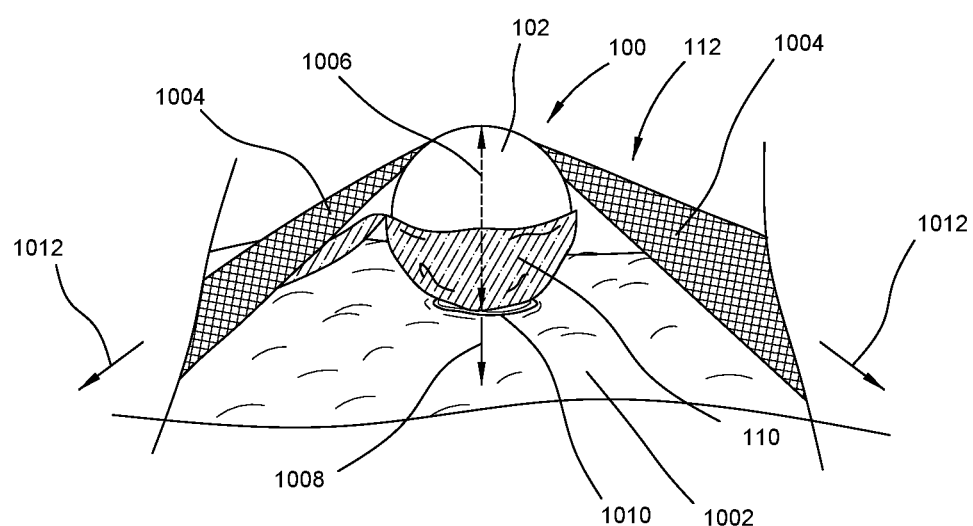
FIG. 10 shows a detail of a deployed trauma dressing article for a junctional injury, in accordance with some embodiments.

FIG. 10 shows a detail of a deployed trauma dressing article 100 for a junctional injury wound site 1010, in accordance with some embodiments. The detail shown here includes a view of the body 102 of the trauma dressing article 100 under the windings 1004 created by the wrap strip 112. The gauze cap 110 is positioned into the wound site 1010 of the person's body 1002. The wrap strip 112 is the wound around the person's body to create several windings 1004. The height 1006 of the body 102 of the trauma dressing article 100 relative to the person's body 1002 and specifically the wound site 1010 under the windings 1004 helps create a force in the direction of arrow 1008 that is greater than if the windings 1004 were simply wound over dressing material placed over the wound site 1010. The force is created by tension 1012 in the windings 1004 which have a net result of pushing or urging the body 102 of the trauma dressing article 100 into the wound site 1010.

Figure 11:
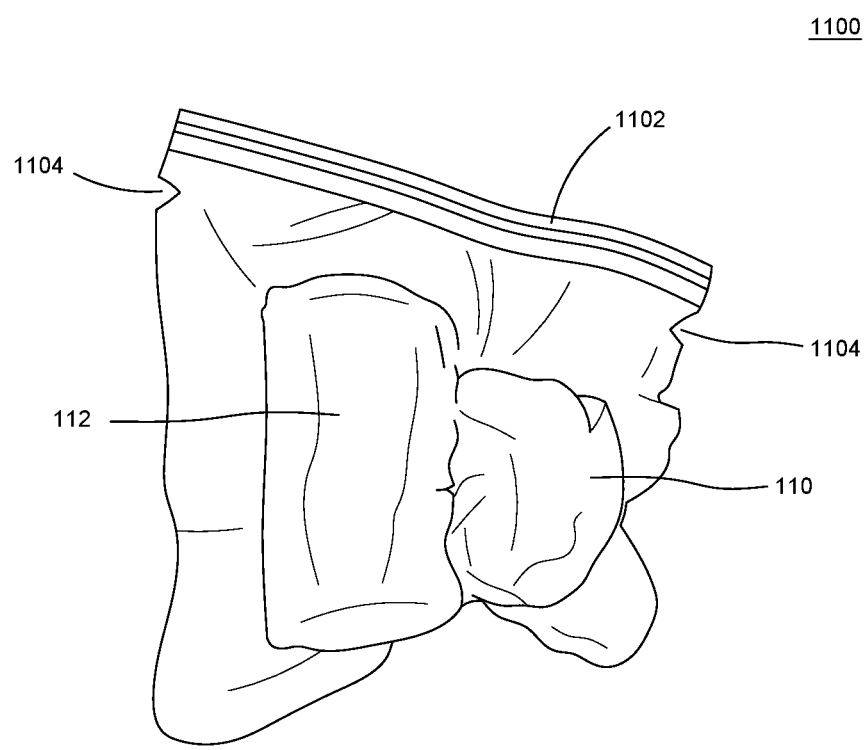
FIG. 11 shows a packaged trauma dressing article for junctional injuries, in accordance with some embodiments.

FIG. 11 shows a packaged trauma dressing article 1100 for junctional injuries, in accordance with some embodiments. In order to provide the trauma dressing article in a sterile condition, it can be packaged in a vacuum sealed package 1102. The vacuum sealed package 1102 can be a rectangular bag sealed on three sides and open at one side. After the trauma dressing article (shown here with the gauze cap 110 and wrap strip 112 in view) is placed inside the bag, the open end of the bag is placed into a vacuum sealer that draws air out of the bag, and when a sufficient vacuum is reached, the open end of the bag is then sealed by a heat treatment that bonds the opposite sides of the bag together. The packaging can include rip notches 1104 that allow a person to rip open the packaging 1102 and remove the trauma dressing article for use. Other forms of packaging can used to package the trauma dressing article, as will occur to those skilled in the art. Since the body with the gauze cap and the wrap strip are packaged together, it is contemplated that in packaged form the wrap strip does not need to be connected to the body.

A trauma dressing article has been disclosed that is particularly suited to prevent exsanguination due to junctional injuries. The disclosed trauma dressing article includes a body having a gauze cap and a wrap strip attached to the body. The gauze cap is placed into the wound site and the wrap strip is used to create windings around the injured person's body and the body of the trauma dressing article, creating pressure against the body of the trauma dressing article into the wound site.

The claims appended hereto are meant to cover all modifications and changes within the scope and spirit of the present invention.

What is claimed is:

1. A trauma dressing article for junctional injuries, comprising:
   a body having a natural uncompressed spherical shape that is made of a-resilient material and having an outer surface, wherein the body includes a first hemisphere and a second hemisphere, wherein the second hemisphere has a radius that is smaller than a radius of the first hemisphere, and wherein the gauze cap covers the second hemisphere and does not extend over the first hemisphere;
   a gauze cap formed over at least a portion of the outer surface of the body and attached to the body; and
   a wrap strip having a first end that is attached to the body, and which extends from the body and wherein the wrap strip is configured to wrap around a human and over the body to compress the body.

2. The trauma dressing article of claim 1, wherein the body has a diameter of one and a half to three inches.

3. The trauma dressing article of claim 1, wherein the wrap strip is self-adhering.

4. The trauma dressing article of claim 1, wherein the wrap strip is elastic.

5. The trauma dressing article of claim 1, wherein the wrap strip is provided in a rolled configuration.

6. The trauma dressing article of claim 1, wherein the wrap strip is at least four feet long.

7. The trauma dressing article of claim 1, wherein the first end of the wrap strip is glued to the body.

8. The trauma dressing article of claim 1, wherein the gauze cap contains a clotting agent that is at least one of kaolin, chitosan, or recombinant activated human clotting factors.

9. The trauma dressing article of claim 1, wherein the gauze cap includes a dressing tail comprising a free section of dressing material that extends freely from the gauze cap.

10. A packaged trauma dressing article, comprising:
    a body having at least a portion of which that is a hemisphere made of a resilient material, and which presents a rounded outer surface, wherein the body is spherical, and includes a first hemisphere and a second hemisphere, wherein the second hemisphere has a radius that is smaller than a radius of the first hemisphere;
    a gauze cap disposed on and covering an outside surface of the second hemisphere made of the resilient material, and wherein the gauze cap covers the second hemisphere and does not extend over the first hemisphere;
    a wrap strip including a sheet strip of dressing wrap having one end attached to the body and a free end, the wrap strip having a length that allows the wrap strip to be wrapped around a junctional location of a person, and further around the person and over the body to compress the body; and
    a packaging in which the body, gauze cap, and wrap strip are disposed and sealed.

11. The packaged trauma dressing article of claim 10, wherein the packaging is vacuum sealed.

12. The packaged trauma dressing article of claim 10, wherein the wrap strip is provided in a rolled configuration.

13. A trauma dressing article for use in junctional injuries to prevent exsanguination, comprising:
    a body having a hemispherical portion made of a resilient material and having an outer surface, wherein the body is spherical, and includes a first hemisphere and a second hemisphere, wherein the second hemisphere has a radius that is smaller than a radius of the first hemisphere,
    an absorbent covering disposed over an outer surface of the second hemisphere; and wherein the absorbent covering covers the second hemisphere and does not extend over the first hemisphere;
    and
    a wrap strip attached to the body, and having a portion that extends from the body to a free end of the wrap strip, wherein the wrap strip is configured to secure the trauma dressing article to a person by wrapping around the person and over the body and thereby compress the body.

14. The trauma dressing article of claim 13, wherein the absorbent covering is a gauze cap that includes a dressing tail comprising a free section of dressing material that extends freely from the gauze cap.

15. The trauma dressing article of claim 14, wherein the gauze cap contains a clotting agent that is at least one of kaolin, chitosan, or recombinant activated human clotting factors.

16. The trauma dressing article of claim 13, wherein the wrap strip is elastic, self-adhering, and configured in a roll.

* * * * *